(12) United States Patent
Chan

(10) Patent No.: US 11,413,256 B2
(45) Date of Patent: Aug. 16, 2022

(54) METHOD FOR TREATING A NEURODEGENERATIVE DISORDER

(71) Applicant: Annji Pharmaceutical Co., Ltd., Taipei (TW)

(72) Inventor: Hardy W. Chan, Redwood City, CA (US)

(73) Assignee: Annji Pharmaceutical Co., Ltd., Taipei (TW)

( * ) Notice: Subject to any disclaimer, the term of this patent is extended or adjusted under 35 U.S.C. 154(b) by 101 days.

(21) Appl. No.: 16/731,794

(22) Filed: Dec. 31, 2019

(65) Prior Publication Data

US 2020/0214997 A1    Jul. 9, 2020

Related U.S. Application Data

(60) Provisional application No. 62/788,566, filed on Jan. 4, 2019.

(51) Int. Cl.
*A61K 31/12*    (2006.01)
*A61P 25/28*    (2006.01)

(52) U.S. Cl.
CPC .............. *A61K 31/12* (2013.01); *A61P 25/28* (2018.01)

(58) Field of Classification Search
CPC ................................. A61K 31/12; A61P 25/28
USPC .......................................................... 514/679
See application file for complete search history.

(56) References Cited

PUBLICATIONS

Fan et al., "Polyglutamine (PolyQ) diseases: genetics to treatments", Cell Transplantation, 2014, 23(4-5), 441-458.
Bertoni et al., "Molecular Bases of Disease: Early and late events induced by PolyQ-expanded proteins: Identification of a common pathogenic property of PolyQ-expanded proteins", The Journal of Biological Chemistry, 2011, 286(6), 4727-41.
Kohen et al., "Oxidation of Biological Systems: Oxidative Stress Phenomena, Antioxidants, Redox Reactions, and Methods for Their Quantification", Toxicologic Pathology, 2002, 30(6), 620-650.
Trachootham et al., "Targeting cancer cells by ROS-mediated mechanisms: a radical therapeutic approach?", Nature Reviews Drug Discovery, Jul. 2009, 8(7), 579-91.
Klockgether et al., "Spinocerebellar ataxia", Nature Reviews Disease Primers, 2019, 5(24), 1-21.
Bargiela et al., "Mitochondrial pathology in progressive cerebellar ataxia", Cerebellum Ataxias, 2015, 2(16), 5 pages.
Ward et al., "Metabolic and Organelle Morphology Defects in Mice and Human Patients Define Spinocerebellar Ataxia Type 7 as a Mitochondrial Disease", Cell Reports, 2019, 26(5), 1189-1202.
Ferrante; Robert J., "Mouse Models of Huntington's Disease and Methodological Considerations for Therapeutic Trials", Biochimica et biophysica acta, 2009, 1792(6), 506-520.
Browne et al., "Oxidative damage in Huntington's Disease Pathogenesis", Antioxidants & Redox Signaling, 2006, 8(11-12), 2061-2073.
Bott et al., "A small-molecule Nrf1 and Nrf2 activator mitigates polyglutamine toxicity in spinal and bulbar muscular atrophy", Human Molecular Genetics, 2016, 25(10), 1979-1989.
Hansen et al., "Changes in Purkinje cell firing and gene expression precede behavioral pathology in a mouse model of SCA2", Human Molecular Genetics, 2013, 22(2), 271-283.
Frank; S., "Treatment of Huntington's Disease", Neurotherapeutics, 2014, 11(1), 153-160.

*Primary Examiner* — Kristin A Vajda
(74) *Attorney, Agent, or Firm* — McDonnell Boehnen Hulbert & Berghoff LLP

(57) ABSTRACT

The invention provides a method for treating a neurodegenerative disorder in a subject in need of such treatment, comprising administrating to said subject a compound with (substituted phenyl)-propenal moiety.

9 Claims, 4 Drawing Sheets

METHOD FOR TREATING A NEURODEGENERATIVE DISORDER

CROSS-REFERENCE TO RELATED APPLICATIONS

This application claims the benefit of priority of U.S. Provisional Patent Application No. 62/788,566, filed Jan. 4, 2019, all of which is incorporated by reference in its entirety.

BACKGROUND

Field of the Disclosure

This invention relates to a method for treating a neurodegenerative disorder. More specifically, the present invention provides a method for treating a neurodegenerative disorder with compounds having at least one (substituted phenyl)-propenal moiety.

Description of Related Art

It is well known that certain natural products may possess therapeutic effects, which has lead to their use in the treatment and prevention of human diseases across many cultures (e.g., Chinese herbal medicines and many other folk medicines). The effectiveness of such treatments has lead the pharmaceutical industry to seek and isolate active compounds from these natural products and develop the active ingredients as therapeutic or prophylactic drugs for the treatment and prevention of a variety of diseases or medical conditions. Thus, many commonly used pharmaceuticals have been developed or have arisen from natural products. However, compounds isolated from natural products are known to play certain physiological function(s) in its native host; whereas their therapeutic effects against human diseases are not readily apparent. Historically, such therapeutic treatments were derived merely by accumulated experiences or "trial and error" in humans. Moreover, because such compounds were not initially created for use in humans, the compounds in their native form are frequently not in the most optimal form, both in structure as well as efficacy, to treat human diseases. However, today's modern chemistry technology, including analytical and synthetic chemistries, together with the advances in medicinal biology have made it possible for one to dissect a chemical structure and localize a "pharmacophore" (a core structure that is essential for the therapeutic activity) within a compound such as one isolated from a natural product; furthermore, these new techniques allow one to synthesize new compounds, based on the structure of a pharmacophore, that possess optimal or even better therapeutic efficacy.

Compound curcumin (existing as a major pigment in a turmeric plant) and many of its analogs have been reported to possess numerous biological activities in vitro, such as, anti-oxidant, anti-inflammatory, anti-tumor, and antiangiogenesis activities; but neither curcumin nor its analogues have been developed into a therapeutic drug to treat human diseases. This indicates curcumin in its native form is probably not an optimal molecule for development into a therapeutic drug.

The polyglutamine (polyQ) diseases are a group of neurodegenerative disorders caused by expanded cytosine-adenine-guanine (CAG) repeats encoding a long polyQ tract in the respective proteins. PolyQ diseases are characterized by the pathological expansion of CAG trinucleotide repeat in the translated region of unrelated genes. The translated polyQ-expanded protein is conformational misfolded and aggregated in the degenerated neurons leading to the dysfunction and degeneration of specific neuronal subpopulations (Fan H. C., Ho L. I., Chi C. S., Chen S. J., Peng G. S., Chan T. M., Lin S. Z., Harn H. J. Polyglutamine (PolyQ) diseases: genetics to treatments. Cell Transplant. 23(4-5): 441-458, 2014). Several pathological mechanisms are observed in poly-Q diseases, including excessive levels of ROS, neuroinflammation, mitochondrial impairment and disturbances in protein homeostasis (proteostasis) (Bertoni A1, Giuliano P, Galgani M, Rotoli D, Ulianich L, Adornetto A, Santillo M R, Porcellini A, Avvedimento V E. Early and late events induced by polyQ-expanded proteins: identification of a common pathogenic property of polyQ-expanded proteins. J Biol Chem. 11; 286(6):4727-41, 2011). To date, a total of nine polyQ disorders in human have been described: spinal and bulbar muscular atrophy (SBMA); six spinocerebellar ataxias (SCA) types 1, 2, 6, 7, 17; Machado-Joseph disease (MJD/SCA3); Huntington's disease (HD); and dentatorubral pallidoluysian atrophy (DRPLA).

An effective treatment for such neurodegenerative disorder is needed.

SUMMARY OF THE DISCLOSURE

The disclosure provides a method for treating a neurodegenerative disorder in a subject in need of such treatment, comprising administrating to said subject a pharmaceutical composition comprising an effective amount of a compound according to formula VIII and optionally a pharmaceutically acceptable carrier or excipient;

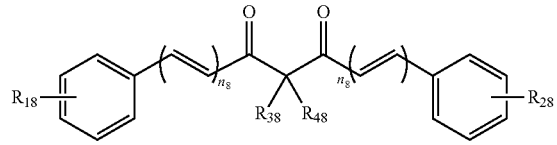

formula VIII wherein
each $R_{18}$ and $R_{28}$ are mono- or di-substituted groups and independently selected from the group consisting of a methoxy group, a hydroxyl group, and an alkyl sulfonyl group;
$R_{38}$ is selected from the group consisting of

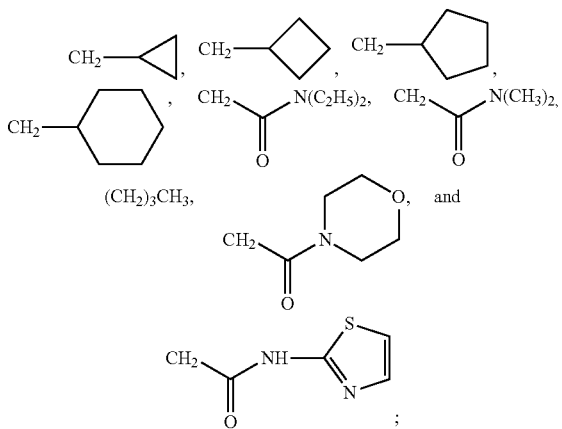

$R_{48}$ is selected from the group consisting of $CH_3$, H, F and Cl; and $n_8$ is 1 or 2.

The present invention is described in detail in the following sections. Other characteristics, purposes and advantages of the present invention can be found in the detailed description and claims.

BRIEF DESCRIPTION OF THE DRAWINGS

The accompanying drawings are included to provide a further understanding of the compositions and methods of the disclosure, and are incorporated in and constitute a part of this specification. The drawings illustrate one or more embodiment(s) of the disclosure and, together with the description, serve to explain the principles and operation of the disclosure.

FIG. 2A shows that ASC-JM17 (JM17) exerts no cytotoxicity on WT and MJD78 cells. Cell viability was assessed by flow cytometry analysis using propidium iodide (PI) to stain dead cells. WT and MJD78 cells were treated with 0.1, 0.3, 0.5, 0.7, 0.9 and 1 µM JM17 (supplemented with 0.005% DMSO) for 24 hours before collected for flow cytometry. Data are presented as the mean±SD. FIG. 2B: Mitochondrial membrane potential of the WT and MJD78 cells was measured using flow cytometric analysis of TMRE staining. WT and MJD78 cells were treated with 0.1, 0.3, 0.5, 0.7, 0.9 and 1 µM JM17 (supplemented with 0.005% DMSO) for 24 hours before collected for flow cytometry. Statistical analysis was achieved using t-test. *p<0.05, compare to WT group; **p<0.01, compare to each DMSO treated group of MJD78 cells. Data are presented as the mean±SD.

DETAILED DESCRIPTION OF THE DISCLOSURE

Figure 1:
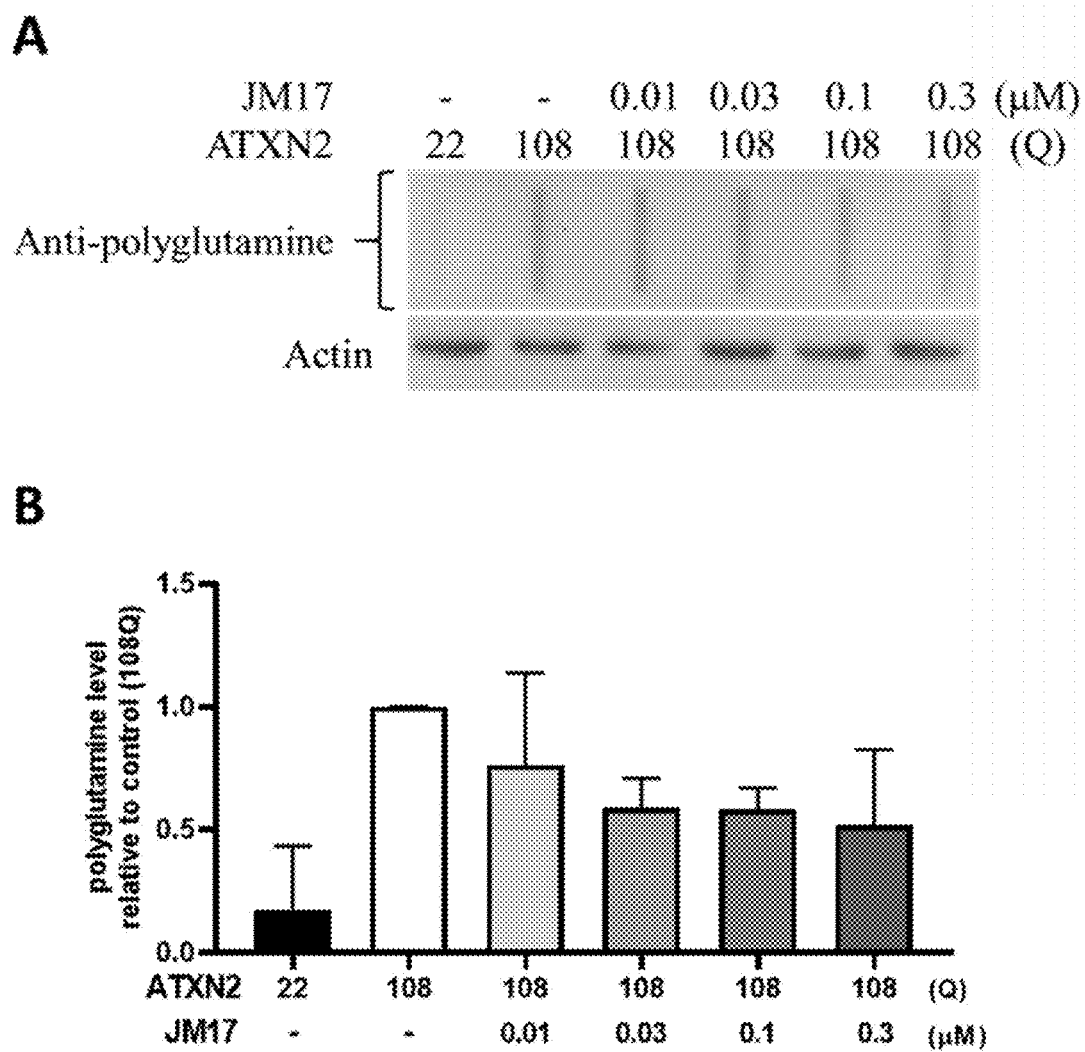
FIG. 1 shows that the polyQ aggregation is suppressed by ASC-JM17 (JM17). (A): Immunoblots of polyQ and actin. The representative blot of three independent experiments. (B): JM17 induced suppression of polyQ aggregation in mutant SH-SY5Y cells (ATXN2-[Q108]) in a dose dependent manner. Each data point represents the mean value and standard deviation of three independent assays. Quantification of the immunoblots was performed using imageJ with relative intensity to control protein (actin) and normalized to ATXN2-[Q108] control treated with vehicle (DMSO).

The present invention can be more readily understood by reference to the following detailed description of various embodiments, the examples, and the chemical drawings and tables with their relevant descriptions. It is to be understood that unless otherwise specifically indicated by the claims, the invention is not limited to specific preparation methods, carriers or formulations, or to particular modes of formulating the compound of the invention into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

The disclosure provides a method for treating a neurodegenerative disorder in a subject in need of such treatment, comprising administrating to said subject a pharmaceutical composition comprising an effective amount of a compound with (substituted phenyl)-propenal moiety, and optionally a pharmaceutically acceptable carrier or excipient. Preferably the compound with (substituted phenyl)-propenal moiety is according to formula VIII:

formula VIII

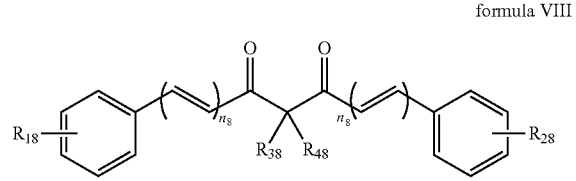

wherein $R_{18}$ and $R_{28}$ are mono- or di-substituted groups and independently selected from the group consisting of a methoxy group, a hydroxyl group, and an alkyl sulfonyl group;

$R_{38}$ is selected from the group consisting of

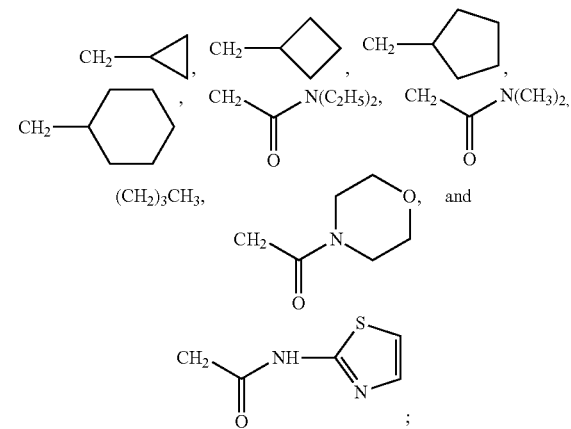

and $R_{48}$ is selected from the group consisting of $CH_3$, H, F and Cl; and $n_8$ is 1 or 2.

The term "(substituted phenyl)-propenal moiety" as used herein refers to a composition including a phenyl group having attached thereto 1) a propenal moiety (when m equals 1) or a penta-2,4-dienal (when m equals 2) and 2) one or two substituents independently selected from: an alkoxy, hydroxy moiety, and an alkyl sulfonyl group. The substitutions may be positioned meta or para or ortho with respect to the propenal moiety as used herein and refers to a general formula

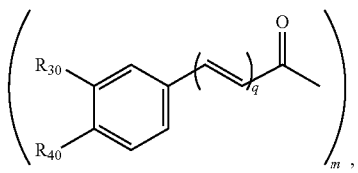

where q may be any number of 1, 2, 3 or 4; and m may be any number of 1, 2, 3, 4, or more.

The term "alkyl" as used herein refers to a straight or branched hydrocarbon chain radical consisting solely of carbon and hydrogen atoms, containing no unsaturation, having from one to ten carbon atoms, and which is attached to the rest of the molecule by a single bond, e.g. methyl, ethyl, n-propyl, 1-methylethyl (iso-propyl), n-butyl, n-pentyl, 1,1-dimethylethyl (t-butyl), and the like.

The term "alkenyl" as used herein refers to a straight or branched hydrocarbon chain radical consisting solely of carbon and hydrogen atoms, containing at least one double bond, having from two to ten carbon atoms, and which is attached to the rest of the molecule by a single bond or a double bond, e.g. ethenyl, prop-1-enyl, pent-1-enyl, penta-1,4-dienyl, and the like.

The term "alkenylene" as used herein refers to a straight or branched hydrocarbon chain which contains a carbon-to-carbon double bond and is represented by the formula $C_pH_{2p-2}$, wherein hydrogen may be replaced by an additional carbon-to-carbon double bond or a monovalent substituent, e.g. ethenylene, prop-1-enylene and the like.

The term "alkoxy" as used herein refers to the radical having the formula —OR wherein R is an alkyl, haloalkyl or cycloalkyl. An "optionally substituted alkoxy" refers to the radical having the formula —OR' wherein R' is an optionally substituted alkyl as described herein.

The term "alkynyl" as used herein refers to a straight or branched hydrocarbon chain radical consisting solely of carbon and hydrogen atoms, containing at least one triple bond, having from two to ten carbon atoms, and which is attached to the rest of the molecule by a single bond or a triple bond, e.g. ethynyl, prop-1-ynyl, but-1-ynyl, pent-1-ynyl, pent-3-ynyl and the like.

The term "aryl" as used herein refers to a radical of carbocyclic ring system wherein at least one of the rings is aromatic. The aryl may be fully aromatic or may contain an aromatic ring in combination with a non-aromatic ring. A "biaryl system" is a compound that includes at least two aryl groups.

The term "cycloalkyl" as used herein refers to a stable monovalent monocyclic or bicyclic hydrocarbon radical consisting solely of carbon and hydrogen atoms, having from three to ten carbon atoms, and which is saturated and attached to the rest of the molecule by a single bond, e.g. cyclopropyl, cyclobutyl, cyclopentyl, cyclohexyl, and the like.

The term "di-ketone bridge," or "ketone-enol bridge" as used herein, refers to a straight or branched hydrocarbon chain including two ketones or an enol positioned in close proximity to a ketone respectively. The "di-ketone bridge" or "ketone-enol bridge" is positioned between at least two aryl moieties.

The term "hydroxyalkyl" as used herein refers to a straight or branched hydroxy substituted hydrocarbon chain radical having from one to ten carbon atoms, e.g. —$CH_2OH$, —$(CH_2)_2OH$, and the like.

In one embodiment of the disclosure, the compounds of formula VIII include 4,4-disubstituted 1,7-bis-(3,4-dimethoxyphenyl)-hepta-1,6-diene-3,5-dione and 6,6-disubstituted 1,11-bis(substituted phenyl)-undeca-1,3,8,10-tetraene-5,7-dione derivatives are as shown in Table 1.

TABLE 1

| Compound ID | $R_{18}$ | $R_{28}$ | $R_{38}$ | $R_{48}$ | $n_8$ | formula |
|---|---|---|---|---|---|---|
| 1 | 3,4-OCH$_3$ | 3'4'-OCH$_3$ | CH$_2$—△ (cyclopropyl) | CH$_3$ | 1 | $C_{28}H_{32}O_6$ 464.55 |
| 2 | 3'4'-OCH$_3$ | 3'4'-OCH$_3$ | CH$_2$—◇ (cyclobutyl) | CH$_3$ | 1 | $C_{29}H_{34}O_6$ 478.5767 |
| 3 | 3'4'-OCH$_3$ | 3'4'-OCH$_3$ | CH$_2$—⬠ (cyclopentyl) | H | 1 | $C_{29}H_{34}O_6$ 478.58 |
| 4 | 3'4'-OCH$_3$ | 3'4'-OCH$_3$ | CH$_2$—⬠ (cyclopentyl) | CH$_3$ | 1 | $C_{30}H_{36}O_6$ 492.60 |

TABLE 1-continued

| Compound ID | $R_{18}$ | $R_{28}$ | $R_{38}$ | $R_{48}$ | $n_8$ | formula |
|---|---|---|---|---|---|---|
| 5 | 3'4'-OCH$_3$ | 3'4'-OCH$_3$ | CH$_2$-cyclohexyl | CH$_3$ | 1 | $C_{31}H_{38}O_6$ 506.63 |
| 6 | 3'4'-OCH$_3$ | 3'4'-OCH$_3$ | CH$_2$-C(=O)-N(C$_2$H$_5$)$_2$ | CH$_3$ | 1 | $C_{30}H_{37}NO_7$ 523.62 |
| 7 | 3'4'-OCH$_3$ | 3'4'-OCH$_3$ | CH$_2$-C(=O)-N(CH$_3$)$_2$ | CH$_3$ | 1 | $C_{28}H_{33}NO_7$ 495.56 |
| 8 | 3'4'-OCH$_3$ | 3'4'-OCH$_3$ | (CH$_2$)$_3$CH$_3$ | CH$_3$ | 1 | $C_{28}H_{34}O_6$ 466.57 |
| 9 | 3'4'-OCH$_3$ | 3'4'-OCH$_3$ | CH$_2$-C(=O)-morpholinyl | H | 1 | $C_{29}H_{33}NO_8$ 523.57 |
| 10 | 3'4'-OCH$_3$ | 3'4'-OCH$_3$ | CH$_2$-C(=O)-NH-thiazol-2-yl | H | 1 | $C_{28}H_{28}N_2O_7S$ 536.60 |
| 11 | 3'4'-CH$_3$ | 3'4'-CH$_3$ | CH$_2$-C(=O)-morpholinyl | CH$_3$ | 1 | $C_{30}H_{35}NO_8$ 537.60 |
| 12 | 3'4'-OCH$_3$ | 3'4'-OCH$_3$ | CH$_2$-C(=O)-NH-thiazol-2-yl | CH$_3$ | 1 | $C_{29}H_{30}N_2O_7S$ 550.62 |
| 13 | 3'4'-OCH$_3$ | 3'4'-OCH$_3$ | CH$_2$-cyclopropyl | F | 1 | $C_{27}H_{29}FO_6$ 468.51 |
| 14 | 3'4'-OCH$_3$ | 3'4'-OCH$_3$ | CH$_2$-cyclobutyl | F | 1 | $C_{28}H_{31}FO_6$ 482.54 |
| 15 | 3'4'-OCH$_3$ | 3'4'-OCH$_3$ | CH$_2$-cyclopentyl | F | 1 | $C_{29}H_{33}FO_6$ 496.57 |
| 16 | 3'4'-OCH$_3$ | 3'4'-OCH$_3$ | CH$_2$-cyclohexyl | F | 1 | $C_{30}H_{35}FO_6$ 510.59 |
| 17 | 3'4'-OCH$_3$ | 3'4'-OCH$_3$ | CH$_2$-C(=O)-N(C$_2$H$_5$)$_2$ | F | 1 | $C_{29}H_{34}FNO_7$ 527.58 |

TABLE 1-continued

| Compound ID | $R_{18}$ | $R_{28}$ | $R_{38}$ | $R_{48}$ | $n_8$ | formula |
|---|---|---|---|---|---|---|
| 18 | 3'4'-OCH$_3$ | 3'4'-OCH$_3$ | CH$_2$C(O)N(CH$_3$)$_2$ | F | 1 | C$_{27}$H$_{30}$FNO$_7$ 499.53 |
| 19 | 3'4'-OCH$_3$ | 3'4'-OCH$_3$ | (CH$_2$)$_3$CH$_3$ | F | 1 | C$_{27}$H$_{31}$FO$_6$ 470.53 |
| 20 | 3'4'-OCH$_3$ | 3'4'-OCH$_3$ | CH$_2$C(O)N(C$_2$H$_5$)$_2$ | Cl | 1 | C$_{29}$H$_{34}$ClNO$_7$ 544.04 |
| 21 | 3'4'-OCH$_3$ | 3'4'-OCH$_3$ | CH$_2$C(O)N(CH$_3$)$_2$ | Cl | 1 | C$_{27}$H$_{30}$ClNO$_7$ 515.98 |
| 22 | 3'4'-OCH$_3$ | 3'4'-OCH$_3$ | CH$_2$CH$_2$COOC$_2$H$_5$ | CH$_3$ | 1 | C$_{29}$H$_{34}$O$_8$ 510.58 |
| 23 | 3'4'-OCH$_3$ | 3'4'-OCH$_3$ | CH$_2$CH$_2$COOC$_2$H$_5$ | F | 1 | C$_{28}$H$_{31}$FO$_8$ 514.54 |
| 24 | 3'4'-OCH$_3$ | 3'4'-OCH$_3$ | CH$_2$CH$_2$COOH | CH$_3$ | 1 | C$_{27}$H$_{30}$O$_8$ 482.52 |
| 25 | 3'4'-OCH$_3$ | 3'4'-OCH$_3$ | CH$_2$CH$_2$COOH | F | 1 | C$_{26}$H$_{27}$FO$_8$ 486.49 |
| 26 | 3'OCH$_3$,4'OH | 3'OCH$_3$,4'OH | CH$_2$CH$_2$COOC$_2$H$_5$ | CH$_3$ | 1 | C$_{27}$H$_{30}$O$_8$ 482.52 |
| 27 | 3'OCH$_3$,4'OH | 3'OCH$_3$,4'OH | CH$_2$CH$_2$COOC$_2$H$_5$ | F | 1 | C$_{26}$H$_{27}$FO$_8$ 486.49 |
| 28 | 3'-OCH$_3$ | 3'-OCH$_3$ | CH$_2$-cyclobutyl | CH$_3$ | 1 | C$_{27}$H$_{30}$O$_4$ 418.52 |
| 29 | 3'-OH | 3'-OH | CH$_2$-cyclobutyl | CH$_3$ | 1 | C$_{25}$H$_{26}$O$_4$ 390.47 |
| 30 | 3'-OCH$_3$ | 3'-OSO$_2$C$_2$H$_5$ | CH$_2$-cyclobutyl | CH$_3$ | 1 | C$_{28}$H$_{32}$O$_6$S 496.62 |
| 31 | 3'-OSO$_2$C$_2$H$_5$ | 3'-OSO$_2$C$_2$H$_5$ | CH$_2$-cyclobutyl | CH$_3$ | 1 | C$_{29}$H$_{34}$O$_8$S$_2$ 574.71 |
| 32 | 3'4'-OCH$_3$ | 3'4'-OCH$_3$ | CH$_2$C(O)N(C$_2$H$_5$)$_2$ | CH$_3$ | 2 | C$_{34}$H$_{41}$NO$_7$ 575.69 |
| 33 | 3'4'-OCH$_3$ | 3'4'-OCH$_3$ | CH$_2$-cyclobutyl | F | 2 | C$_{32}$H$_{35}$FO$_6$ 534.62 |
| 34 | 3'4'-OCH$_3$ | 3'4'-OCH$_3$ | CH$_2$-cyclobutyl | H | 1 | C$_{28}$H$_{32}$O$_6$ 464.55 |

In another embodiment of the disclosure, the compound of formula VIII is wherein $R_{18}$ and $R_{28}$ are di-substituted methoxy groups, $R_{38}$ is

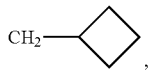

$R_{48}$ is H, and $n_8$ is 1, referred throughout as ASC-JM17 or JM17.

The disclosure also provides a composition comprising the compound with (substituted phenyl)-propenal moiety. The composition according to the disclosure, in certain embodiments, is a pharmaceutical composition, food composition or a cosmetic composition.

In certain embodiments, the composition according to the disclosure is a pharmaceutical composition comprising the compound with (substituted phenyl)-propenal moiety and a pharmaceutically acceptable carrier and/or excipient.

In certain embodiments, the pharmaceutical composition comprises an effective amount of the compound.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "subject" as used herein denotes any animal, preferably a mammal, and more preferably a human. The examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "treating" or "treatment" as used herein denotes reversing, alleviating, inhibiting the progress of, or improving the disorder, disease or condition to which such term applies, or one or more symptoms of such disorder, disease or condition.

The term "carrier" or "excipient" as used herein refers to any substance, not itself a therapeutic agent, used as a carrier and/or diluent and/or adjuvant, or vehicle for delivery of a therapeutic agent to a subject or added to a formulation to improve its handling or storage properties or to permit or facilitate formation of a dose unit of the composition into a discrete article such as a capsule or tablet suitable for oral administration. Suitable carriers or excipients are well known to persons of ordinary skill in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials (such as cellulose esters of alkanoic acids and cellulose alkyl esters), low melting wax cocoa butter, amino acids, urea, alcohols, ascorbic acid, phospholipids, proteins (for example, serum albumin), ethylenediamine tetraacetic acid (EDTA), dimethyl sulfoxide (DMSO), sodium chloride or other salts, liposomes, mannitol, sorbitol, glycerol or powder, polymers (such as polyvinyl-pyrrolidone, polyvinyl alcohol, and polyethylene glycols), and other pharmaceutically acceptable materials. The carrier should not destroy the pharmacological activity of the therapeutic agent and should be non-toxic when administered in doses sufficient to deliver a therapeutic amount of the agent.

The pharmaceutical composition according to the disclosure is administered by any method known in the art, including, but not limited to, intramuscular, intradermal, intravenous, subcutaneous, intraperitoneal, intranasal, oral, mucosal or external routes. The appropriate route, formulation and administration schedule can be determined by those skilled in the art. In the present disclosure, the pharmaceutical composition can be formulated in various ways, according to the corresponding route of administration, such as a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream or a combination thereof. If necessary, it may be sterilized or mixed with any pharmaceutically acceptable carrier or excipient, many of which are known to one of ordinary skill in the art.

The external route as used herein is also known as local administration, includes but is not limited to administration by insufflation and inhalation. Examples of various types of preparation for local administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets or liposome or microencapsulation preparations.

Ointments, creams and gels, may, for example, be formulated with an aqueous or oily base with the addition of suitable thickening and/or gelling agent and/or solvents.

Such bases may thus, for example, include water and/or oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Spray compositions may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution. The aerosol composition may optionally contain additional formulation excipients well known in the art such as surfactants e.g. oleic acid or lecithin and cosolvents e.g. ethanol.

Topical preparations may be administered by one or more applications per day to the affected area; over the skin areas occlusive dressings may advantageously be used. Continuous or prolonged delivery may be achieved by an adhesive reservoir system.

The cosmetic composition according to the disclosure may be an aqueous phase formulation consisting essentially of water; it may also comprise a mixture of water and of water-miscible solvent (miscibility in water of greater than 50% by weight at 25° C.), for instance lower monoalcohols containing from 1 to 5 carbon atoms such as ethanol or isopropanol, glycols containing from 2 to 8 carbon atoms, such as propylene glycol, ethylene glycol, 1,3-butylene glycol or dipropylene glycol, C3-C4 ketones and C2-C4 aldehydes, and glycerin. Such an aqueous formulation preferably is in a form of aqueous gel or hydrogel formulation. The hydrogel formulation comprises a thickening agent to thicken the liquid solution. Examples of the thickening agents include, but are not limited to, carbomers, cellulose base materials, gums, algin, agar, pectins, carrageenan, gelatin, mineral or modified mineral thickeners, polyethylene glycol and polyalcohols, polyacrylamide and other polymeric thickeners. The thickening agents which give the stability and optimal flow characteristics of the composition may be used.

The cosmetic composition according to the present disclosure may be in a form of emulsion or cream formulation. It can contain emulsifying surfactants. These surfactants may be chosen from anionic and nonionic surfactants. Reference may be made to the document "Encyclopedia of Chemical Technology, Kirk-Othmer", volume 22, pp. 333-432, 3rd edition, 1979, Wiley, for the definition of the properties and functions (emulsifying) of surfactants, in particular pp. 347-377 of said reference, for the anionic and nonionic surfactants.

The surfactants used in the cosmetic composition according to the disclosure are chosen from: nonionic surfactants: fatty acids, fatty alcohols, polyethoxylated or polyglycerolated fatty alcohols such as polyethoxylated stearyl or cetyl-stearyl alcohol, fatty acid esters of sucrose, alkylglucose esters, in particular polyoxyethylenated fatty esters of C1-C6 alkyl glucose, and mixtures thereof; anionic surfactants: C16-C30 fatty acids neutralized with amines, aqueous ammonia or alkaline salts, and mixtures thereof. Surfactants which make it possible to obtain an oil-in-water or wax-in-water emulsion may be used.

The cosmetic composition according to the disclosure may further comprise an effective amount of a physiologically acceptable antioxidant selected from the group consisting of butylated p-cresol, butylated hydroquinone monomethyl ether, and a tocopherol.

The cosmetic composition according to the disclosure may further comprise natural or modified amino acid, natural or modified sterol compound, natural or modified collagen, silk protein or soy protein.

The cosmetic composition according to the disclosure is formulated for topical application to keratin materials such as the skin, the hair, the eyelashes or the nails. They may be in any presentation form normally used for this type of application, especially in the form of an aqueous or oily solution, an oil-in-water or water-in-oil emulsion, a silicone emulsion, a microemulsion or nanoemulsion, an aqueous or oily gel or a liquid, pasty or solid anhydrous product.

The cosmetic composition according to the disclosure may be more or less fluid and may have the appearance of a white or colored cream, an ointment, a milk, a lotion, a serum, a paste, a mousse or a gel. It may optionally be topically applied onto the skin in the form of an aerosol, a patch or a powder. It may also be in solid form, for example, in the form of a stick. It may be used as care products and/or as makeup products for the skin. Alternatively, it may be formulated as shampoos or conditioners.

In known fashion, the cosmetic composition according to the disclosure may also contain additives and adjuvants that are common in cosmetics, such as hydrophilic or lipophilic gelling agents, preservatives, antioxidants, solvents, fragrances, fillers, pigments, odor absorbers and dyestuffs.

The compound can be added to a conventional food composition (i.e. the edible food or drink or precursors thereof) in the manufacturing process of the food composition. Almost all food compositions can be supplemented with the compound of the disclosure. The food compositions that can be supplemented with the compound of the disclosure include, but are not limited to, candies, baked goods, ice creams, dairy products, sweet and flavor snacks, snack bars, meal replacement products, fast foods, soups, pastas, noodles, canned foods, frozen foods, dried foods, refrigerated foods, oils and fats, baby foods, or soft foods painted on breads, or mixtures thereof.

The disclosure also provides a method for treating a neurodegenerative disorder in a subject in need of such treatment, comprising administrating to said subject the pharmaceutical composition as mentioned above.

While not wishing to be limited by theory, it is Applicant's belief that the method according to the disclosure is treating the neurodegenerative disorder through turning on heat shock response. The activation of the heat shock response (HSR) is known to remediate toxic protein conformations.

While not wishing to be limited by theory, it is Applicant's belief that the method according to the disclosure is treating the neurodegenerative disorder through facilitating the correct protein folding.

While not wishing to be limited by theory, it is Applicant's belief that the method according to the disclosure is treating the neurodegenerative disorder through activating nuclear factor-erythroid 2 p45-related factor 2 (Nrf2). The compound with (substituted phenyl)-propenal moiety can activate a transcriptional factor Nrf2 (nuclear factor-erythroid 2 p45-related factor 2).

While not wishing to be limited by theory, it is Applicant's belief that the method according to the disclosure is treating the neurodegenerative disorder through upregulating anti-oxidant defenses.

While not wishing to be limited by theory, it is Applicant's belief that the method according to the disclosure is treating the neurodegenerative disorder through changing mitochondrial function. In most of polyQ disease cells, the misfolded proteins/aggregates coupled with mitochondrial defect induces high level of ROS.

While not wishing to be limited by theory, it is Applicant's belief that the method according to the disclosure is treating the neurodegenerative disorder through maintaining protein homeostasis.

While not wishing to be limited by theory, it is Applicant's belief that the method according to the disclosure is treating the neurodegenerative disorder through activating anti-oxidant effect.

The reduction-oxidation (redox) state is used to describe the balance of GSH/GSSG, $NAD^+$/NADH and $NADP^+$/NADPH in a biological system such as a cell or organ. The redox state is reflected in the balance of several sets of metabolites, whose interconversion is dependent on these ratios. An abnormal redox state resulted from polyQ-expanded protein misfolding and aggregation can develop in a variety of deleterious situations. Free radical reactions are redox reactions that occur as a part of homeostasis and killing microorganisms, where an electron detaches from a molecule and then reattaches almost instantaneously. ROS are a part of redox molecules and can become harmful to the human body if they do not reattach to the redox molecule or an antioxidant (R Kohen, A Nyska, Oxidation of Biological Systems: Oxidative Stress Phenomena, Antioxidants, Redox Reactions, and Methods for Their Quantification. Toxicologic pathology, 30(6): 620-650, 2002; Trachootham D, Alexandre J, Huang P. Targeting cancer cells by ROS-mediated mechanisms: a radical therapeutic approach? Nat Rev Drug Discov. July; 8(7):579-91, 2009). Misfolded protein and ROS induction dominantly damage the neuronal cell of polyQ diseases (Bertoni A1, Giuliano P, Galgani M, Rotoli D, Ulianich L, Adornetto A, Santillo M R, Porcellini A, Avvedimento V E. Early and late events induced by polyQ-expanded proteins: identification of a common pathogenic property of polyQ-expanded proteins. J Biol Chem. 11; 286(6):4727-41, 2011). The compound with (substituted phenyl)-propenal moiety is a redox regulator modulating the redox homeostasis in cells.

In one embodiment of the disclosure, the neurodegenerative disease is polyQ diseases. The polyQ disease includes, but is not limited to, spinal and bulbar muscular atrophy (SBMA), spinal muscular atrophy (SMA), Huntington's disease (HD), Machado-Joseph disease (MJD/SCA3), spinocerebellar ataxias (SCA) type 1, spinocerebellar ataxias (SCA) type 2, spinocerebellar ataxias (SCA) type 6, spinocerebellar ataxias (SCA) type 7, spinocerebellar ataxias (SCA) type 17, or dentatorubral-pallidoluysian atrophy (DRPLA).

In one embodiment of the methods of the disclosure, the neurodegenerative disorder is Huntington's disease. In one embodiment of the methods of the disclosure, the neurodegenerative disorder of the disclosure, the neurodegenerative disorder of the disclosure is spinocerebellar ataxia (any type).

While not wishing to be limited by theory, it is Applicant's belief that the proposed mode of action of the compound with (substituted phenyl)-propenal moiety is concerned with two cytotoxic pathways contributing to spinocerebellar ataxias.

The first mechanism is associated with the stress caused by the mutant protein that bears the abnormally long polyQ sequences, known as a polyglutamine tract. During protein synthesis, the expanded CAG repeats in affected genes are translated into a series of uninterrupted glutamine residues forming what is known as a polyglutamine tract. Such extended polyglutamine tracts may cause significant changes in protein structure that in turn lead to the loss of function, increased aggregation and/or result in the abnormal activation of downstream signaling pathways (Klockgether T, Mariotti C, Paulson H L. Spinocerebellar ataxia. *Nat Rev Dis Primers.* 2019; 5(1):24). If unrestrained, these intracellular events cause prominent damage to cerebellar Purkinje neurons with consecutive cerebellar atrophy. Other parts of the nervous system, such as the spinal cord, basal ganglia and pontine nuclei in the brainstem, can be involved as well.

Another pathway is related to the oxidative stress caused by the impaired mitochondria function. The dysfunction of mitochondria has been detected in a quarter of all people with the disease (Bargiela D, Shanmugarajah P, Lo C, et al. Mitochondrial pathology in progressive cerebellar ataxia. *Cerebellum Ataxias.* 2015; 2:16-16). Although histochemical changes suggestive of mitochondrial pathology were not obvious in the muscle biopsies of patients with genetically confirmed SCA14, SCA28 and SCA35, a recent report by Ward et al. demonstrates an altered metabolism and mitochondrial dysfunction in SCAT patients, mice, and human stem cell derived neurons (Ward J M, Stoyas C A, Switonski P M, et al. Metabolic and Organelle Morphology Defects in Mice and Human Patients Define Spinocerebellar Ataxia Type 7 as a Mitochondrial Disease. *Cell reports.* 2019; 26(5): 1189-1202.e1186).

While not wishing to be limited by theory, it is Applicant's belief that the proposed mode of action of the compound with (substituted phenyl)-propenal moiety is concerned with the following mechanisms contributing to Huntington's disease. In general, the mechanisms through which mutant protein aggregation can lead to neurodegeneration are largely unknown but the disease pathogenesis could be attributed to proteolysis of mHTT, resulting in abnormal and toxic protein aggregates in neurons. Although these aggregates induce chaperones and become ubiquitinated, they persist, indicating protein misfolding and failed proteolysis. This affects protein homeostasis since accumulation of mHTT aggregates sequester other important cellular proteins such as chaperones, proteasomal proteins, normal HTT and transcription factors. Evidence suggests direct interactions between mHTT and transcription factors as a defect causing transcriptional dysfunction. This results in events such as oxidative stress, mitochondrial dysfunction, altered receptor activities, inflammation, pro-apoptotic signals, bioenergetic defects, increased transglutaminase activity and excitotoxicity, all ultimately leading to neuronal death (Ferrante R J. Mouse Models of Huntington's Disease and Methodological Considerations for Therapeutic Trials. *Biochimica et biophysica acta.* 2009; 1792(6): 506-520).

The mitochondrial dysfunction induced oxidative stress has been implicated in HD patients (Browne S E, Beal M F. Oxidative damage in Huntington's disease pathogenesis. *Antioxid Redox Signal.* 2006; 8(11-12):2061-2073). Moreover, the defects in mitochondrial complex II, III, and IV were also observed in striatum of postmortem HD brain (Bott L C, Badders N M, Chen K-L, et al. A small-molecule Nrf1 and Nrf2 activator mitigates polyglutamine toxicity in spinal and bulbar muscular atrophy. *Human molecular genetics*. 2016; 25(10):1979-1989). In certain embodiments, the compound of the disclosure activates the Nrf2 antioxidant pathway to increase expression of antioxidant enzymes. Specifically, the compound of the disclosure increases the expression of antioxidant enzymes HO-1, Nqo1, Gclc and catalase. Knocking down expression of Nrf2 prevented induction of HO-1 and Nqo1 in response to the compound with (substituted is phenyl)-propenal moiety.

In another aspect, in one embodiment of the disclosure, the neurodegenerative disease is protein aggregate-neurodegenerative diseases.

The protein aggregate-neurodegenerative disease includes, but is not limited to, amyotrophic lateral sclerosis (ALS), Alzheimer's disease (AD), Parkinson's disease (PD), multiple system atrophy (MSA), Lewy body disease, Frontotemporal dementia, corticobasal degeneration (CBD), motor neuron disease, Prion disease or progressive supranuclear palsy (PSP).

The following examples are provided to aid those skilled in the art in practicing the present invention.

EXAMPLES

Example 1: Spinocerebellar Ataxias Model

JM17 Suppresses PolyQ Aggregation in Neuronal SH-SY5Y Cells

Abnormal accumulation of misfolded and aggerated mutant proteins, a hallmark of SCA, reflects imbalances in the cellular network that governs protein synthesis, folding, transport and degradation. This network is controlled by multiple signaling pathways to minimize damage to macromolecules and organelles in response to extrinsic and intrinsic stressors (Klockgether T, Mariotti C, Paulson H L. Spinocerebellar ataxia. *Nat Rev Dis Primers*. 2019; 5(1):24).

The neuronal SH-SY5Y cells overexpressing mutant ataxin-2, were used to assess the ability of one of the compounds of the disclosure, JM17, to activate pathways aimed at reducing aggregate accumulation. These cells were treated with JM17 for 24 hours and polyQ aggregation was assayed by filtered retardation assay and quantitative immunoblotting. As shown in FIG. 1, cells expressing ataxin-2 with the most common extension in human population (extension of 22Q) have very little, if any, measurable aggregates. However, the ataxin-2 aggregates are readily detectable in cells expressing ataxin-2 with the 108Q extension. Further, the results of these experiments summarized FIG. 1B, demonstrate that JM17 reduced formation of ataxin-2 with the 108Q extension aggregates in a dose dependent manner.

JM17 Repairs Dysfunctional Mitochondria in SCA3 In Vitro Model

Previous studies have demonstrated that mitochondrial abnormality/dysfunction is associated with neurodegenerative diseases, including SCA (Klockgether T, Mariotti C, Paulson H L. Spinocerebellar ataxia. *Nat Rev Dis Primers*. 2019; 5(1):24).

Figure 2A:
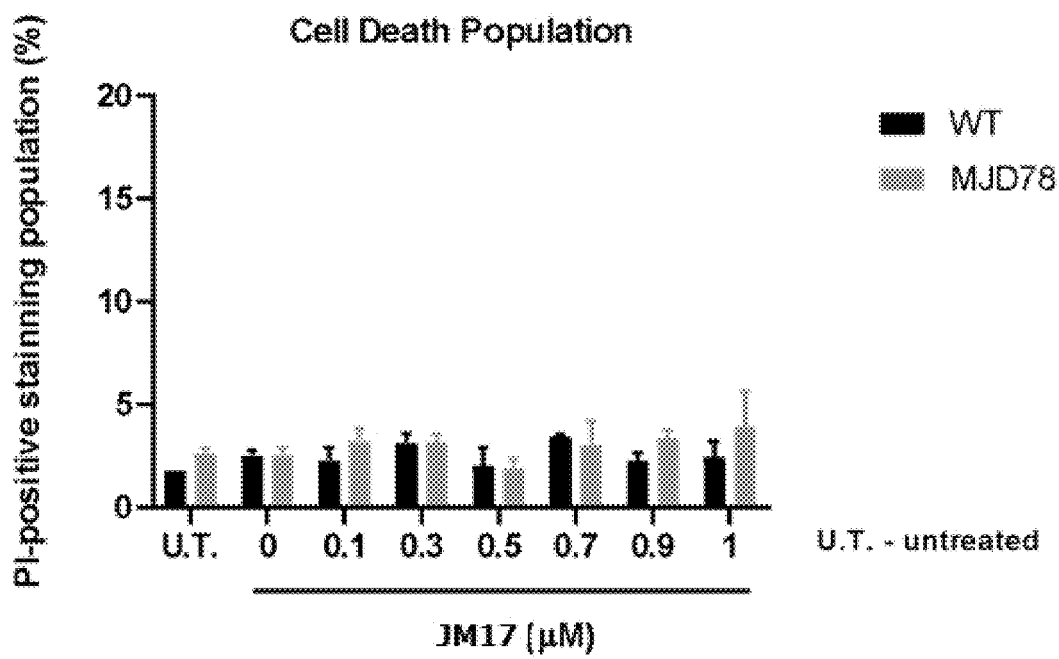
FIGS. 2A and 2B show that ASC-JM17 (JM17) improves the dysfunctional mitochondrial membrane potential of MJD78 cells.

To investigate the potential of JM17 as a treatment for SCA3, an in vitro cell model system was used, in which SK-N-SH neuroblastoma cells were transfected with constructs overexpressing green fluorescence protein (GFP)-tagged full-length ATXN3 with 78 glutamine residues (ataxin-3-78Q-GFP), termed MJD78 cells hereafter. In the experiment, mitochondrial activity was evaluated in wild type and MJD78 cells with or without JM17 treatment by flow cytometric analysis of tetramethylrhodamine ethyl ester (TMRE) staining. The cytotoxicity effects of JM17 were measured using propidium iodide (PI) to stain dead cells. Both wild type and MJD78 cells were treated with 0.1, 0.3, 0.5, 0.7, 0.9 and 1 µM JM17 for 24 hours and the results showed that neither wild type nor MJD78 cells had any signs of cytotoxicity, following such treatment (FIG. 2A).

Figure 2B:
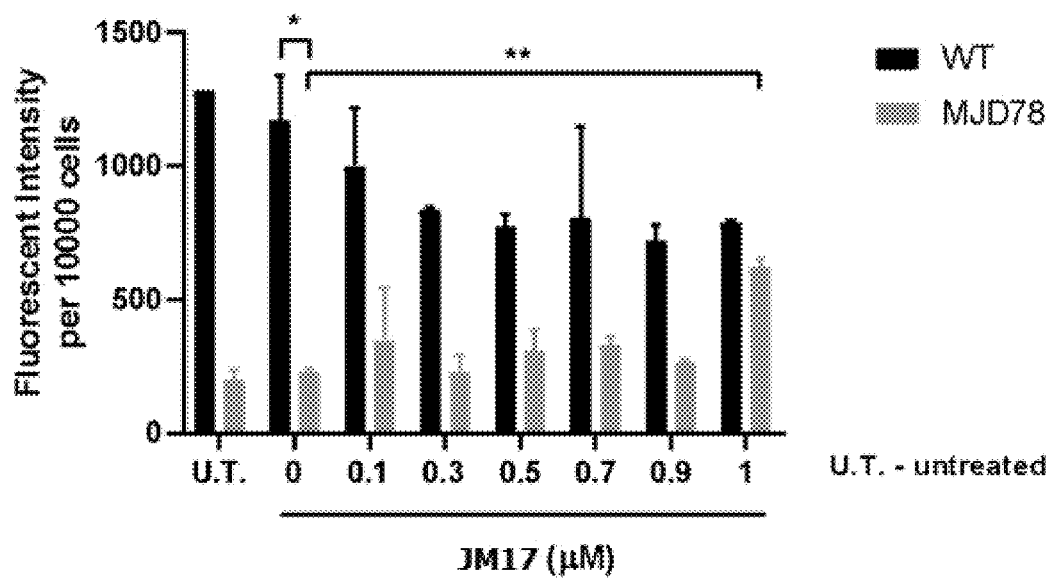

The mitochondrial membrane potential of wild type cells treated with JM17 at 1 µM dose was decreased by 20-30%, which is possibly due to JM17 mediated metabolism alteration. However, MJD78 cells had an opposite effect, where the treatment with JM17 at the same dose has increased the mitochondrial membrane potential by 2 to 2.5-fold compared to DMSO treated MJD78 cells (FIG. 2B).

JM17 Improves Motor Coordination in SCA2 Animal Model

To investigate the pharmacological efficacy of JM17 in SCA2, a mouse model with a 127-glutamine track on ataxin-2 was employed (Hansen S T, Meera P, Otis T S, Pulst S M. Changes in Purkinje cell firing and gene expression precede behavioral pathology in a mouse model of SCA2. *Hum Mol Genet*. 2013; 22(2):271-283). This model is well characterized and has been shown to recapitulate SCA human phenotype in that the motor function is normal in young animals, but is progressively declined with age.

The experiments were performed as follows. Experimental mice (nine and seven mice per group) were given JM17 orally. Assuming diet intake $\frac{1}{10}$ of the mice's body weight every day, appropriate amount of JM17 was thoroughly mixed into pulverized standard rodent chow at the low dose of 40 mg/kg and high dose of 120 mg/kg daily starting at the age of 6 weeks. The control group, composed of nine SCA2 transgene animals matched by age and weight to the experimental mice, was receiving placebo. Another control group was composed of eleven animals with age/weight matching the wild type mice. Beginning at the week 9, the motor coordination of every mice was assessed two times per week by accelerating rotarod test. These assessments continued until the mice reached the age of 40 weeks.

Figure 3:
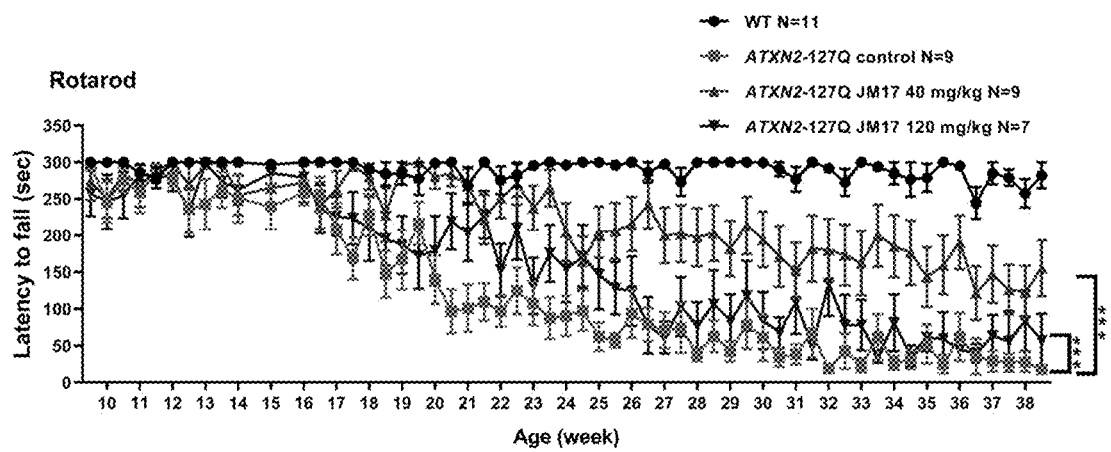
FIG. 3 shows that ASC-JM17 (JM17) delays the progression of the SCA related loss of motor coordination in the SCA animal model. Motor coordination of wildtype, SCA2 mice, and SCA2 mice fed with JM17 40 mg/kg and 120 mg/kg per day was monitored using Rotarod test from week 9 to week 40.

FIG. 3 shows the results of the rotarod test expressed as the retention time on the spinning disk. As expected, at the age of about 17 weeks SCA2 mice began losing their motor skills, which continued to deteriorate later. Importantly, the control group resembling wild type mice did not have any measurable loss of motor function. This phenotype of SCA2 transgene mice is consistent with the age dependent loss of motor coordination in SCA patients, thus validating the animal model used to assess JM17 efficacy in SCA. Further, SCA2 mice dosed with JM17 at 40 mg/kg per day demonstrated significant improvement on rotarod test performance as compared to the SCA2 control mice. Firstly, the 40 mg/kg per day JM17 treatment delayed the onset of the clinical manifestation of SCA (from about weeks 15-17 to about weeks 22-24). Secondly, the rate of decline was hampered by the JM17 and treated animals performed significantly better than untreated control group even at week 40 (FIG. 3, $p<0.001$, two-way ANOVA). The group dosed with JM17 at 120 mg/kg per day, also showed delayed SCA progression and performed better than control group in the time window between weeks 20 and 26, however this advantage was lost as the mice aged (FIG. 3). Although the additional studies will help to find the optimal treatment regiments, currently available data, taken together show that JM17 treatment delays the progression of the SCA related loss of motor function in validated models of the disease.

In conclusion, experimental data strongly support that SCA patients may benefit from JM17 treatment. First, JM17 reduced toxic aggregation of protein bearing polyQ tracks. Second, experimental in vitro SCA3 cell model demonstrates a positive effect of JM17 on the improvement of dysfunctional mitochondrial activity. Finally, experiments with the SCA animal model provide compelling evidence that JM17 treatment reduces progression of the disease as measured by the clinically meaningful assessment of the age-related loss of motor function.

Example 2: Huntington's Disease Model

JM17 Demonstrates Efficacy in Animal Model of HD

HD is a progressive neurodegenerative disease. This disorder is caused by the expansion of the CAG trinucleotide repeat sequence in the huntingtin gene, and it has been postulated that the altered protein leads to a loss of medium spiny neurons in the striatum (Frank S. Treatment of Huntington's disease. *Neurotherapeutics*. 2014; 11(1):153-160). As the first transgenic model for HD, R6/2 mouse contains an N-terminal fragment of HTT (exon 1) with approximately 144-150 CAG repeats at exon 1. It exhibits a progressive homogenous HD-like phenotype, with survival ranging 14 to 21 weeks. Recent findings suggest that this model exhibits progressive HD-like behavioral and neuropathological phenotype that corresponds more closely to human HD, thus providing support that the R6/2 mouse is an appropriate model for testing potential therapies for HD (Ferrante R J. Mouse Models of Huntington's Disease and Methodological Considerations for Therapeutic Trials. *Biochimica et biophysica acta*. 2009; 1792(6):506-520). Additionally, the HTT aggregates are present postnatal day 1 and increase in number and size with age, suggesting disease onset and progression occur before clinical phenomena (Ferrante R J. Mouse Models of Huntington's Disease and Methodological Considerations for Therapeutic Trials. *Biochimica et biophysica acta*. 2009; 1792(6):506-520).

As a result, to assess the pathophysiological relevance of the neuroprotective action of JM17 in vivo, the sponsor employed the R6/2 mouse model of the disease. The main findings are detailed below.

The R6/2 mice were given a feed containing JM17 or vehicle at a final concentration of 120 mg/kg daily from the age of 6 to 13.5 weeks. The mice were tested for a) motor function/locomotor activity and b) brain volume. In HD, loss of motor function and reduction in brain volume, specifically of the striatum and cortex areas, are hallmark features of disease progression (Frank S. Treatment of Huntington's disease. *Neurotherapeutics*. 2014; 11(1):153-160).

Figure 4:
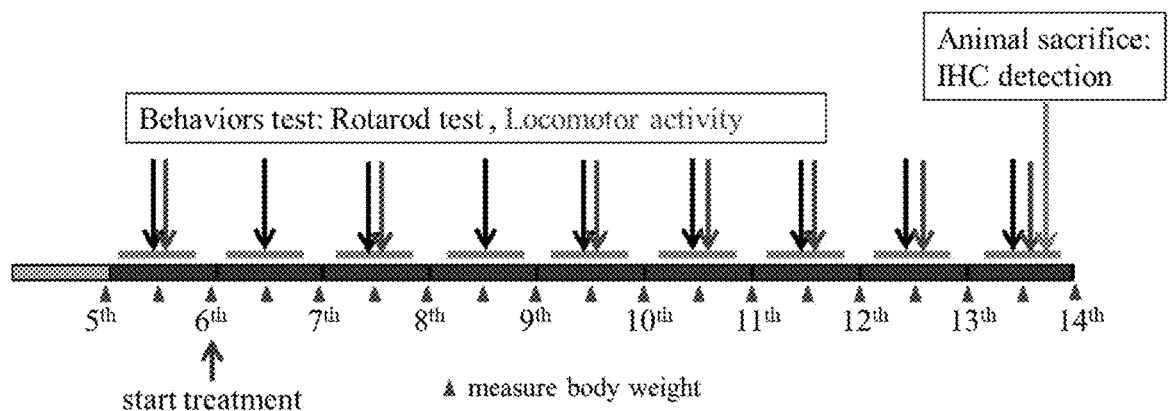
FIG. 4 shows illustration of the experimental flowchart in animal model of Huntington disease. IHC=Immunohistochemistry.

The experimental setup is shown in FIG. 4. The body weight, the ability to remain on a rotating rod (rotarod test), and locomotor activity were recorded weekly from the age of 5 to 14 weeks. The MRI for brain volume was analyzed at 13.5 weeks of age.

Figure 5:
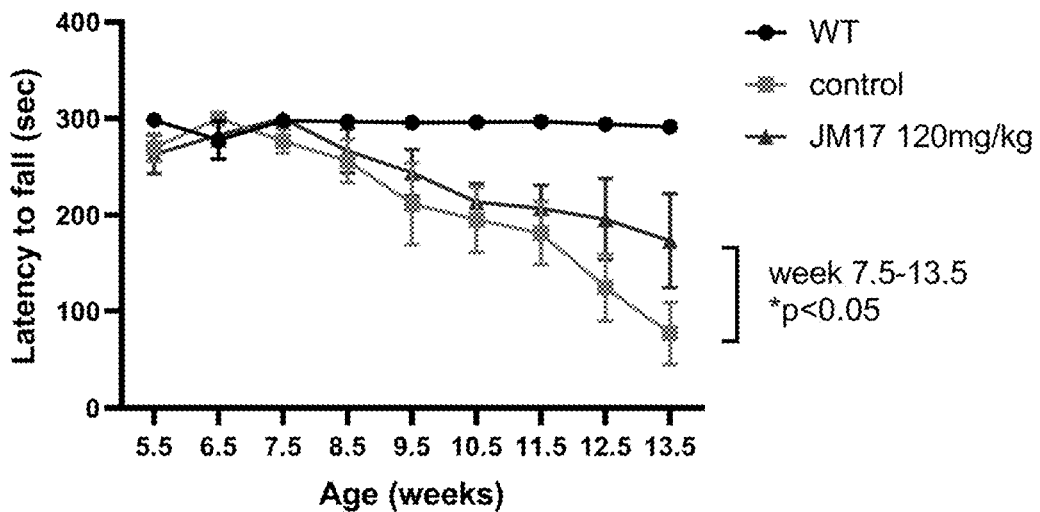
FIG. 5 shows that ASC-JM17 (JM17) ameliorates disease phenotype in HD mice model. Latency to fall from Rotarod of wild type (n=5) and HD mice treated with vehicle (n=5) or 120 mg/kg (n=5) daily in feed from 6 to 13.5 weeks of age was shown. Data were expressed as mean±SEM. *p<0.05 (two-way ANOVA from week 7.5 to 13.5).

Although there were no statistical differences in body weight and locomotor activity between the JM17 and control group, there was a statistically significant improvement in the rotarod performance of mice that received JM17 as compared to vehicle control (FIG. 5).

This demonstrates that JM17 can halt progression of motor function defects that are associated with HD.

Figure 6:
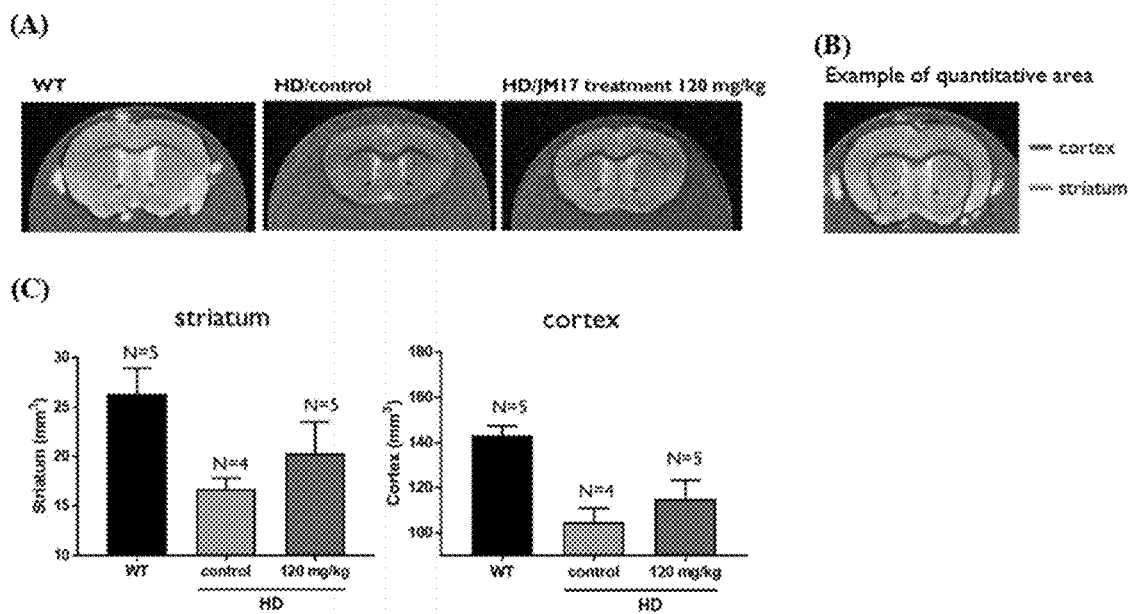
FIG. 6 shows MRI assessment of brain volume. There are 9 sequential images in MRI assessment for each brain. (A) The representative MRI image on brain of wild-type (WT, left), vehicle control (middle) and 120 mg/kg of JM17 treatment (right) groups. (B) The quantitative area for the size of striatum (green circle of the image) and cortex (blue circle of the image) was shown. (C) The quantitative results of striatum and cortex size. Data was expressed by as mean±SD.

As an additional measurement of JM17 efficacy in HD treatment, brain volume was measured by MRI at the end of treatment (13.5 weeks). The average volume of striatum and cortex in JM17 treatment group increased as compared to the vehicle control group (FIG. 6).

This demonstrates that JM17 can reduce neuronal loss from the cortex and striatum areas of the brain.

Taken together, both sets of data, reduction in motor disease progression and loss of neurons in the brain, strongly support that JM17 has the potential to treat HD.

While the present invention has been described in conjunction with the specific embodiments set forth above, many alternatives thereto and modifications and variations thereof will be apparent to those of ordinary skill in the art. All such alternatives, modifications and variations are regarded as falling within the scope of the present invention.

What is claimed is:

1. A method for treating a neurodegenerative disorder in a subject in need of such treatment, comprising administrating to said subject a pharmaceutical composition comprising an effective amount of a compound according to formula VIII, and optionally a pharmaceutically acceptable carrier or excipient;

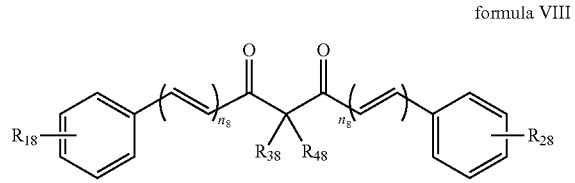

formula VIII wherein each $R_{18}$ and $R_{28}$ are mono- or di-substituted groups and independently selected from the group consisting of a methoxy group, a hydroxyl group, and an alkyl sulfonyl group;

$R_{38}$ is selected from the group consisting of

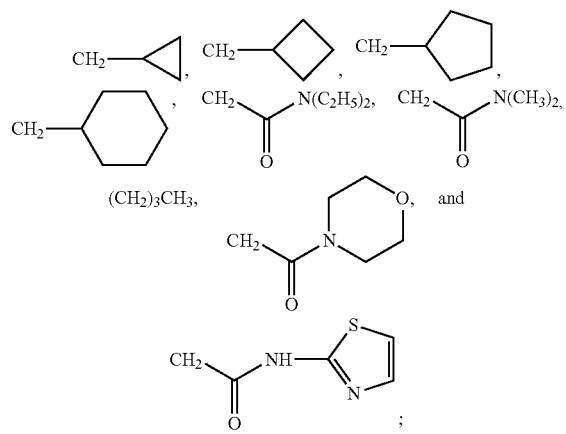

$R_{48}$ is selected from the group consisting of $CH_3$, H, F and Cl; and $n_8$ is 1 or 2;

wherein the neurodegenerative disorder is spinocerebellar ataxia, Huntington's disease, or amyotrophic lateral sclerosis.

2. The method according to claim 1, wherein $R_{18}$ and $R_{28}$ are di-substituted methoxy groups, $R_{38}$ is

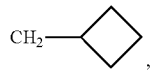

, $R_{48}$ is H, and $n_8$ is 1.

3. The method according to claim 1, wherein the treatment of the neurodegenerative disorder is through turning on heat shock response.

4. The method according to claim 3, wherein the treatment of the neurodegenerative disorder is through facilitating the correct protein folding.

5. The method according to claim 1, wherein the treatment of the neurodegenerative disorder is through activating nuclear factor-erythroid 2 p45-related factor 2 (Nrf2).

6. The method according to claim 5, wherein the treatment of the neurodegenerative disorder is through upregulating anti-oxidant defenses.

7. The method according to claim 5, wherein the treatment of the neurodegenerative disorder is through changing mitochondrial function.

8. The method according to claim 5, wherein the treatment of the neurodegenerative disorder is through maintaining protein homeostasis.

9. The method according to claim 5, wherein the treatment of the neurodegenerative disorder is through activating anti-oxidant effect.

* * * * *